United States Patent [19]
Selker

[11] Patent Number: 5,276,612
[45] Date of Patent: Jan. 4, 1994

[54] RISK MANAGEMENT SYSTEM FOR USE WITH CARDIAC PATIENTS

[75] Inventor: Harry P. Selker, Wellesley, Mass.

[73] Assignee: New England Medical Center Hospitals, Inc., Boston, Mass.

[21] Appl. No.: 586,252

[22] Filed: Sep. 21, 1990

[51] Int. Cl.$^5$ ............................................. G06F 15/42
[52] U.S. Cl. ............................... 364/413.06; 128/668
[58] Field of Search ................. 364/413.06; 128/668; 395/100, 101, 149

[56] References Cited

U.S. PATENT DOCUMENTS

| | | | |
|---|---|---|---|
| 3,608,545 | 9/1971 | Novack et al. | 128/2.06 |
| 3,937,004 | 2/1976 | Natori et al. | 128/672 |
| 4,181,135 | 1/1980 | Andreson et al. | 128/703 |
| 4,230,125 | 10/1980 | Schneider | 128/670 |
| 4,315,309 | 2/1982 | Coli | 364/200 |
| 4,347,851 | 9/1982 | Jundanian | 128/668 |
| 4,404,974 | 9/1983 | Titus | 128/670 |
| 4,422,081 | 12/1983 | Woods | 128/710 |
| 4,457,315 | 7/1984 | Bennish | 128/704 |
| 4,664,125 | 5/1987 | Pinto | 128/672 |
| 4,679,144 | 7/1987 | Cox et al. | 364/417 |
| 4,680,708 | 7/1987 | Ambos et al. | 364/417 |
| 4,754,762 | 7/1988 | Stuchl | 128/696 |
| 4,957,115 | 9/1990 | Selker | 128/696 |
| 4,974,598 | 12/1990 | John | 128/696 |
| 5,054,493 | 10/1991 | Cohn et al. | 128/672 |

FOREIGN PATENT DOCUMENTS 599407 11/1987 Australia .

OTHER PUBLICATIONS

"Computer Edges Doctor in Heart Cases", Corey Dean, The New York Times, Mar. 31, 1988.
M. W. Pozen et al., "A Predictive Instrument To Improve Coronary-Care-Unit Admission Practices In Acute Ishemic Heart Disease", New England Journal of Medicine, vol. 310, May 17, 1984, pp. 1273-1278.
J. T. Bigger, Jr., et al., "The Relationships Among Ventricular Arrythmias, Left Ventricular Dysfunction, and Mortality in the Two Years After Myocardial Infarction", 1985 Yearbook of Cardiology, pp. 170-172.
J. Mukharji et al., "Risk Factors for Sudden Death After Acute Myocardial Infarction: Two-Year Follow-Up", 1985 Yearbook of Cardiology, pp. 172-173.
B. A. Cohen et al., "Automated electroencephalographic analysis as a prognostic indicator in stroke", Med. & Biol. Eng. & Comput., 1977, pp. 431-437.
W. Sherman et al., "Thrombolysis in Acute Myocardial Infarction", Cardiology Update, Reviews for Physicians, 1986, pp. 117-135.

*Primary Examiner*—Gail O. Hayes
*Attorney, Agent, or Firm*—Fish & Richardson

[57] ABSTRACT

A risk management system for use in a health care facility which receives patients who may be experiencing cardiac problems, the system including a first input port for receiving inputs derived from electrocardiograph measurements of a patient; a predictive instrument for using the inputs to compute a probability of the patient having a particular heart condition; a printer for generating a risk management form reporting the computed probability for the patient as well as other clinical and ECG-related observations for the patient, the form also containing categories requiring a person who is evaluating the patient to enter additional information relating to the evaluation of the patient, the computed probability triggering the printer to generate the form only when the computed probability falls within a preselected range which is less than the total range of possible values for the computed probability.

19 Claims, 3 Drawing Sheets

Chest Pain or Possible MI Checklist  ← 100

Age: _____
Sex: ☐ Male   ☐ Female

Chest or Left Arm
    Pain/Discomfort*:  ☐ Yes, Chief Complaint   ☐ Yes, NOT Chief Complaint   ☐ No

Chief Complaint if not Chest Discomfort: _____

Characteristics of Chest Pain or Chief Complaint:
    Character: _____  Duration: _____
    Made worse by: _____ Relieved by: _____
    Suggestive of ischemia:  ☐ Yes   ☐ Somewhat   ☐ No
    Comments: _____

**Patient reports prior heart attack*:**  ☐ Yes   ☐ No

**Patient reports prior NTG use*:**  ☐ Yes   ☐ No

Electrocardiographic Findings (Excluding AVR):

Chest Pain at time of ECG:  ☐ Yes   ☐ Yes but improved   ☐ No

Rhythm:  ☐ NSR   ☐ AF/SVT   ☐ VT/VF   ☐ Other: __

Q Waves:  ☐ None
        ☐ Poor R wave progression
        ☐ Yes, but only one or only "insignificant" Q waves
        ☐ Yes, two or more significant Q waves ST Segments*:  ☐ No abnormalities
        ☐ Straightening or depression/elevation < 1mm in two or more leads
        ☐ Elevation or depression ≥ 1mm in two or more leads T Waves*:  ☐ No abnormalities
        ☐ Flat or inverted < 1mm in two or more leads
        ☐ Inverted ≥ 1 mm in two or more leads
        ☐ "Hyperacute" (Peaked and at least 50% of R wave amplitude) in two or more leads Other:  ☐ PVCs   ☐ LVH   ☐ Bundle Branch Block   ☐ Other: _____

Compared to Prior ECG: ☐ No Changes   ☐ Changes: _____
        ☐ Prior ECG not available   ☐ Prior ECG not requested

Probability of Acute Cardiac Ischemia from Predictive Instrument _____ %  ← 110

Triage Decision:  ☐ CCU/ICU   ☐ Intermediate Care   ☐ Ward   ☐ Home

Special instructions if sent home: _____

Follow up instructions: _____

FIG. 2

| VARIABLE | COEFFICIENTS (bi) | | VALUES (xi)* |
|---|---|---|---|
| CONSTANT (b₀) | -3.933 | | |
| CPAIN | 1.231 | Chest or left arm pain/pressure present<br>Not present | 1<br>0 |
| SX1CPAIN | 0.882 | Chest or left arm pain chief complaint<br>Otherwise | 1<br>0 |
| MALESEX | 0.712 | Male<br>Female | 1<br>0 |
| AGE | -1.441 | Patient age 40 or less<br>Otherwise | 1<br>0 |
| AGE50 | 0.667 | Patient age greater than 50<br>Otherwise | 1<br>0 |
| SEXAGE50 | -0.426 | Male patient age greater than 50<br>Otherwise | 1<br>0 |
| QWAVE | 0.616 | ECG Q waves present<br>Otherwise | 1<br>0 |
| STEL | 0.314 | ECG S-T segment elevated 2mm or more<br>ECG S-T segment elevated 1-2mm<br>Otherwise | 2<br>1<br>0 |
| STDEP | 0.993 | ECG S-T segment depressed 2mm or more<br>ECG S-T segment depressed 1-2mm<br>ECG S-T segment depressed 0.5-1mm<br>Otherwise | 2<br>1<br>0.5<br>0 |
| TWEL | 0.095 | ECG T waves elevated ("hyperacute")<br>Otherwise | 1<br>0 |
| TWINV | 1.127 | ECG T-waves inverted 5mm or more<br>ECG T-waves inverted 1-5mm<br>ECG T-waves flat<br>Otherwise | 2<br>1<br>0.5<br>0 |
| TWISTDEP | -0.314 | Both STDEP and TWINV not 0<br>Otherwise | 1<br>0 |

FIG. 3

RISK MANAGEMENT SYSTEM FOR USE WITH CARDIAC PATIENTS

BACKGROUND OF THE INVENTION

The invention relates to a risk management system for use in a health care delivery environment.

In response to the increasing costs of providing medical care and the growing risks of expensive medical malpractice litigation, risk management has grown in importance to hospital administrators, often accounting for a sizable commitment of hospital resources to achieve its objectives. In general, hospital personnel responsible for risk management programs have two primary objectives. One of their objectives is to identify those areas of greatest exposure for the hospital due to, among other things, a real risk of actual medical malpractice or the lack of procedures or evidence of having followed procedures that would satisfy a reasonable standard of due care such as might be required to provide an adequate defense against a groundless malpractice claim. The other objective follows from the first. It is to implement those changes in hospital practice or procedures which will reduce the hospital's exposure, beginning with the areas of greatest exposure. The changes may involve, for example, taking steps to make sure that actual medical malpractice does not occur or even just making sure that adherence to acceptable standards of due care has taken place and can be proven.

The importance of such risk management programs is particularly recognized by the insurance carriers who insure the hospital against financial losses due to such exposure. It is generally the insurance carrier that must pay the high expenses of malpractice litigation, regardless of whether the claim is actually justified or ultimately proves to be groundless. It is also the insurance carrier which pays the judgements that arise out of such litigation. Predictably, the premiums which the hospital pays to its medical malpractice carrier reflects the amount of exposure the hospital has to such claims. And, not surprisingly, the level of those premiums often depends very much on the seriousness with which the hospital takes its risk management responsibilities.

SUMMARY OF THE INVENTION

In general, in one aspect, the invention is a risk management system for use in a health care facility which receives patients who may be experiencing cardiac problems. The system includes a first input port for receiving inputs derived from electrocardiograph measurements of a patient; a predictive instrument for using the inputs to compute a probability of the patient having a particular heart condition; a printer for generating a risk management form reporting the computed probability for the patient as well as other clinical and ECG-related observations for the patient. The form also contains categories requiring a person who is evaluating the patient to enter additional information relating to the evaluation of the patient. The computed probability triggers the printer to generate the form only when the computed probability falls within a preselected range which is less than the total range of possible values for the computed probability.

Preferred embodiments include the following features. The system further includes an electrocardiograph for generating an electrocardiograph waveform for the patient; and a waveform analyzer for analyzing the electrocardiograph waveform and generating the electrocardiograph-derived inputs. The particular heart condition is acute cardiac ischemia. The preselected range may include all possible probabilities above a preselected positive non zero lower limit or it may include less than all probabilities above the lower limit (e.g., from about b 5% to about 55%). In addition, the system includes a second input port for receiving inputs relating to clinical data for the patient and the predictive instrument is adapted to use said clinical data inputs along with the electrocardiograph-derived inputs to compute the probability of acute cardiac ischemia. Further, the system includes means for enabling a user to cause the printer to generate the form independent of what the value of the computed probability is.

Also in preferred embodiments, the predictive instrument uses an empirically based mathematical model of actual clinical experience to compute the probability of acute cardiac ischemia. In particular, the predictive instrument uses a multivariate logistic regression model to compute the probability of acute cardiac ischemia.

In general, in another aspect, the invention is a method for managing risk in a health care environment which receives patients who may be experiencing cardiac problems. The method includes using an electrocardiograph to measure a patient's condition; generating input signals from electrocardiograph measurements of the patient's condition; using a predictive instrument to compute from the input signal the probability that the patient is experiencing a particular heart condition; using the computed probability to trigger the generation of a risk management form reporting the computed probability for the patient as well as other clinical and ECG-related observations for the patient. The form also contains categories requiring a person who is evaluating the patient to enter additional information relating to the evaluation of the patient. The computed probability triggers the printer to generate the form only when the computed probability falls within a preselected range which is less than the total range of possible values for the computed probability.

An advantage of the risk management system is that it generates a patient evaluation form only for those cardiac patients in triage for whom there is a greater risk of a subsequent challenge to the correctness of the admit/release decision. The form is generated in real time, before making the decision to admit or release, and it documents some of the information which provided the basis for the admit/release decision including, for example, the computed probability of acute cardiac ischemia and other clinical and ECG findings.

The form serves several advantageous functions including preserving evidence of the basis upon which the admit/release decision was made and flagging a subgroup of patients for whom there may be greater risks in being challenged for having made an erroneous decision. In addition, the form serves to encourage the doctor to take special care in deciding how to handle patients for whom the admit/release decision is a close call. The risk management system has the additional advantage of not generating forms for categories of cardiac patients for whom documenting the admit/release decision is not very useful. Therefore, it does not unnecessarily add to the burden of medical staff.

Other advantages and features will become apparent from the following description of the preferred embodiment and from the claims.

DESCRIPTION OF THE PREFERRED EMBODIMENT

FIG. 2 illustrates the documentation generated by the risk management system; and FIG. 3 is a list of the coefficient values for the predictive instrument used within the system of FIG. 1; and

STRUCTURE AND OPERATION

Figure 1:
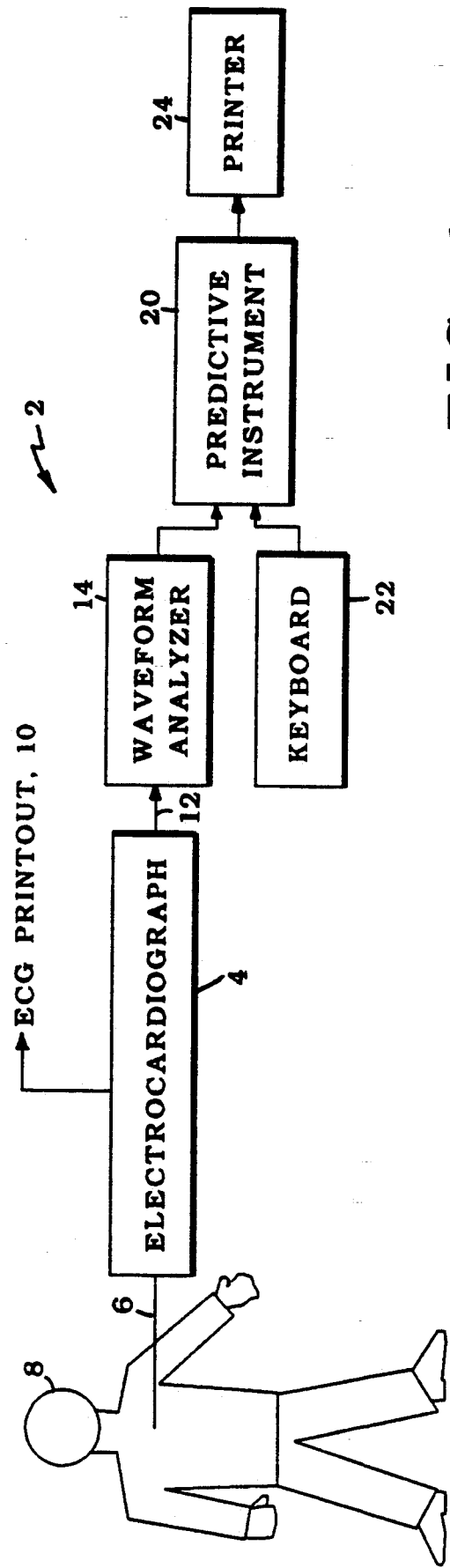
FIG. 1 is a block diagram of a risk management system.

Referring to FIG. 1, in a risk management system 2 for use in a triage unit of a hospital, for example, an electrocardiograph 4 having electrodes 6 monitors the cardiac activity of a patient 8 who is suspected of having a heart problem. Electrocardiograph 4 produces an ECG trace 10 of the patient's cardiac activity and it generates twelve output signals 12 from the signals received through electrodes 6. A waveform analyzer 14 receives output signals 12 and analyzes their waveforms for predetermined characteristics, such as the presence of Q waves, the presence and level of elevation and/or depression of S-T segments, the presence of elevated T waves, and/or the presence of inverted or flat T waves. Analyzer 14 digitally encodes the results of its analysis to generate a feature recognition signal 16, which is sent to a predictive instrument 20.

Some commercially available computer-assisted electrocardiograph's combine the functions of both electrocardiograph 4 and waveform analyzer 14 and thus could be used for electrocardiograph 4 and waveform analyzer 14. An HP (Hewlett Packard) Pagewriter is one such example. The signal analyzer portion of such equipment can be programmed, using, for example, the ElectroCardiograph Language (ECL) which is also available from HP, to recognize whether the lead-based signals from the electrocardiograph contain particular features. Or, it may be programmed to identify the location of the myocardial infarction (MI) based upon the presence of certain identifiable waveform characteristics.

The individual in triage who is performing an initial evaluation of the patient, such as a nurse, determines other relevant clinical information from patient 8 and inputs this information into predictive instrument 20 through a keyboard 22. The other relevant clinical information includes, for example, the patient's age and sex, whether the patient is experiencing chest or left arm pain or pressure, and whether chest or left arm pain is the patient's chief complaint.

Based upon recognition signal 16 and the clinical information input through keyboard 22, predictive instrument 20 computes a probability that patient 8 is experiencing acute cardiac ischemia. To perform this computation, predictive instrument 20 employs an empirically-based, mathematical model that predicts the likelihood of acute cardiac ischemia for that patient that is represented by a multivariate logistic regression equation of the following form:

$$P = 100[1 - (1+e^z)^{-1}] \quad \text{(Eq. 1)}$$

$$Z = b_0 + \Sigma_i b_i X_i \quad \text{(Eq. 2)}$$

where

P is the probability of acute cardiac ischemia;

$X_i$ for $1 \leq i \leq n$, are n independent ECG and clinical variables;

$b_0$ is an intercept coefficient; and $b_i$ is the coefficient of the $i^{th}$ independent variable $X_i$.

When the computed probability falls within a predetermined range (e.g., from 5% to 55%), predictive instrument 20 causes a printer 22 to output a risk management form 100 such as shown in FIG. 2. If the computed probability falls outside the preselected range, risk management system 2 produces the ECG trace for the patient and reports the computed probability but does not generate form 100 for that patient. System 2 may include a feature which permits the nurse to trigger system 2 to generate form 100 even for patients whose computed probability falls outside the preselected range or which automatically generates form 100 for all patients who report a particular symptom (e.g., those patients whose primary complaint is chest or left arm pain or discomfort). Form 100 then accompanies the patient throughout the remainder of his evaluation and is ultimately incorporated into the patient's medical records.

Form 100 reports the probability of acute ischemia as computed by predictive instrument 20 (see field 110). It also includes other information or requests for information in several categories relevant to the admission/release decision. For example, form 100 reports the results of the electrocardiograph under the heading "Electrocardiographic Findings". Some of the entries in this area of form 100 are automatically entered by predictive instrument 20 (e.g., the measurements relating to Q waves, ST segments and T waves) and appear on the generated form. Other entries are made by a nurse or a doctor who evaluates the patient.

Form 100 also automatically reports clinical information such as that which was required by predictive instrument 20 to compute the probability of cardiac ischemia for the patient. This category of information includes the patient's age and sex, and whether or not the patient complained of chest or left arm pain or discomfort.

Form 100 includes additional categories which must be filled out by somebody during the evaluation of the patient and which request information that is deemed necessary for a complete evaluation of the patient. Some of these categories are filled out by the nurse who initially evaluates the patient, while others are filled out by a doctor to whom the patient is directed after the initial evaluation. For example, either the nurse or the doctor provides a written description of the patient's chief complaint under the category entitled "Chief Complaint if not Chest Discomfort", provides a written description of the pain symptoms under the category entitled "Characteristics of Chest Pain or Chief Complaint", and checks off boxes indicating whether the patient reported prior heart attacks, has been using nitroglycerine, or was experiencing chest pain at the time of the electrocardiograph. Furthermore, form 100 requires the doctor to evaluate the patient's ECG and report his conclusions as to the patient's heart rhythm (e.g., NSR, AF/SVT, VT/VF, or other) and diagnose the presence of other cardiac problems (e.g., PVCs, LVH, Bundle Branch Block, other). These items are chosen to enhance the appropriate evaluation of the patient and to provide documentation of important features that are often valuable in cases of malpractice litigation.

Finally, form 100 contains portions for reporting the results of the evaluation. There is a place for reporting the triage decision as to whether the patient is to be admitted and, if admitted, what type of care the patient should receive (i.e., intensive care, intermediate care or ward). There is another place for describing the instructions given to the patient.

The probability of acute cardiac ischemia reported on form 100 provides an important measure of the seriousness of the patient's condition and thus will typically be a significant factor in deciding whether or not admission is indicated for the patient. The advisability of admission increases as the probability rises. When the probability rises above a certain level (e.g., 55%), the likelihood that the patient will be admitted approaches 100%. On the other hand, when the probability falls below another level (e.g., 5-10%), the likelihood of the patient being released from the health care facility approaches 100%. These levels, although based on data gathered at multiple hospitals to date, of course, are not hard thresholds but may vary to reflect the experience derived through use of predictive instrument 20 in a hospital environment.

The preselected range of probabilities which triggers the printing of documentation is chosen so as to encompass those individuals for whom the probability of having a myocardial infarction if they are sent home is not negligible (e.g., those above 5% probability of acute ischemia) and it excludes those patients for whom there is little chance that they will be sent home (e.g., those above 55%). That is, the preselected range covers those patients for whom documentation of the admission/release decision is most necessary from a risk management perspective. The criteria which establish the thresholds at either end of the preselected range reflect a balancing of the costs and burdens of generating and processing extra documentation against the benefits that will be achieved by using and maintaining such documentation. Thus, the thresholds reflect the circumstances and experience of the particular health care provider in which the risk management system is used and may be altered.

In the emergency room environment, one of the costs of using such documentation is that it imposes added burdens on often already heavily burdened emergency room staff. It is desirable to avoid adding more work (such as filling out unnecessary forms) on staff that already has its hands full treating patients under crisis conditions. Furthermore, requiring forms where staff perceives them to be often unnecessary for a significant percentage of the patient population increases the chances that the documentation will not be generated for the patients for whom it is most appropriate.

Counterbalancing these costs, there at least three readily identifiable benefits. First, the generation of documentation for a subset of heart patients flags those patients as different from the general population of heart patients. Flagging those patients and requiring the doctor to process and fill in documentation for those patients, triggers a cognitive interaction that encourages more self conscious evaluation of that patient by the doctor thereby reducing the risk of erroneous decision. That is, the documentation helps reduce the risk of an incorrect decision to release the patient where the risk of an incorrect decision may tend to be higher. Secondly, flagging those patients also aids in quality assurance. It makes it easier for a third party, namely, the hospital, to identify the group of higher risk patients and to evaluate the admit/release decisions that are made for that group and to provide feedback to the doctor on how to improve his future evaluations when appropriate. Third, the document records the basis of the admission/release decision for a subgroup of cardiac patients who constitute the greatest risk of malpractice liability for an improper release decision. Thus, the documentation preserves evidence of the basis for the admission/release decision for possible use in defending against charges that the release should not have been allowed. Providing risk management of this type also reduces the cost of malpractice insurance.

The actual coefficients used in Eq. 1 are shown in FIG. 3. Standard logistic regression modeling was done using the BMDP LR and SAS Logist programs, using the maximum likelihood method for estimating the coefficients. See, for example, N. C. Cary in SUGI Supplement Library User's Guide, SAS Institute, p. 181-202, 1983, and L. Engelman, "PLR Stepwise Logistic Regression," BMDP Statistical Software, Chap. 14.5, pp. 330-334, BMDP publishers, Westwood, Calif. The coefficients were based upon prospectively-collected clinical data for 3453 hospital emergency room patients seen in New England hospitals for chest pain, shortness of breath, or other symptoms suggestive of heart disease.

Referring to FIG. 3, the left column identifies the name of the variable $X_i$, the center column specifies the value of the coefficient $b_i$ corresponding to the named variable, and the right column identifies the values which the variable $X_i$ may assume. Note that only the largest value for an $X_i$ is used per variable. Also, ECG findings must be present in at least two leads (S-T segment and T wave changes are "normal" if they are secondary to right or left complete bundle branch blocks, left ventricular hypertrophy, or a paced QRS). Only one type of abnormality is coded each for S-T segment and for T wave per patient (exclusive of TWISTDEP), with elevation taking priority. Deviations are expressed in mm, using the standard ECG scale of 1 mm=0.1 mV.

When prospectively applied to 2320 emergency room patients, predictive instrument 20 yielded excellent diagnostic performance. Its receiver-operating characteristic (ROC) curve was 0.88 and its ROC curve path suggests performance comparable to that of physicians. (Indeed, evidence from clinical trials has shown that when combined with clinical judgement of physicians, the resulting diagnostic accuracy is better than either the predictive instrument or the physician alone.) The slope of the relationship between predicted and observed likelihoods of having acute ischemia was 1.11 and the regression's $R^2$ was 0.97. (A slope of 1.0 would reflect perfect calibration.) The correlation coefficient for the relationship of the predictive instrument's predicted and actual proportions of acute ischemia was 0.99 ($P<0.0001$).

Other embodiments are within the following claims.

What is claimed is:

1. A risk management system for use in a health care facility which receives patients who may be experiencing cardiac problems, the system comprising;
   a first input port receiving inputs derived from electrocardiograph measurements of a selected one of said patients;
   a second input port receiving user entered information about the selected patient;
   a predictive instrument using the inputs to compute a probability of the selected patient having a particular heart condition;

a printer means for generating a risk management form reporting the computed probability as well as other clinical and ECG-related observations for the selected patient, said printer means programmed to also print a set of uncompleted categories on said form, said set of uncompleted categories being the same regardless of what user entered information has been provided prior to generating said form, said uncompleted categories to be filled in with additional information relating to the evaluation of the selected patient by persons who evaluate the selected patient and said set of uncompleted categories selected to enhance medical evaluations of said patients when completed by said persons subsequent to the printing of said form, said predictive instrument automatically triggering said printer means to generate said form when and only when said computed probability falls within a preselected range which is less than the total range of possible values for said computed probability.

2. The system of claim 1 further comprising:
an electrocardiograph for generating an electrocardiograph waveform for the patient; and
a waveform analyzer for analyzing the electrocardiograph waveform and generating the electrocardiograph-derived inputs.

3. The system of claim 1 or 2 wherein said particular heart condition is acute cardiac ischemia.

4. The system of claim 1 wherein the preselected range includes all possible probabilities above a preselected positive non zero lower limit.

5. The system of claim 1 wherein the preselected range only extends from about 5% to about 55%.

6. The system of claim 3 wherein said predictive instrument uses an empirically based mathematical model of actual clinical experience to compute the probability of acute cardiac ischemia.

7. The system of claim 6 wherein said predictive instrument uses a regression model to compute the probability of acute cardiac ischemia.

8. The system of claim 7 wherein said predictive instrument uses a multivariate logistic regression model to compute the probability of acute cardiac ischemia.

9. The system of claim 1 further comprising a second input port for receiving inputs relating to clinical data for the patient and wherein said predictive instrument uses said clinical data inputs along with said electrocardiograph-derived inputs to compute the probability of the patient having a particular heart condition.

10. The system of claim 1 further comprising means for enabling a user to cause said printer to generate said form independent of what the value of said computed probability is.

11. A method for managing risk in a health care environment which receives patients who may be experiencing cardiac problems, the method comprising:
using an electrocardiograph to measure a condition of a selected one of said patients;
supplying other information about the selected patient;
generating input signals from electrocardiograph measurements of the patient's condition;
computing from the input signals and from at least some of the other information supplied for the selected patient a probability that the selected patient is experiencing a particular heart condition;
automatically generating a risk management form reporting the computed probability as well as other clinical and ECG-related observations for the selected patient, said form also containing a set of uncompleted categories, said set of uncompleted categories being the same regardless of which of said patients is the selected patient and regardless of said other information that has been supplied prior to generating said form, said uncompleted categories to be filled in with additional information related to the evaluation of the select ed patient by persons who evaluate the selected patient and said set of uncompleted categories selected to enhance a medical evaluation of said patients when completed by said persons subsequent to the printing of said form, said form being automatically generated when and only when said computed probability falls within a preselected range which is less than the total range of possible values for said computed probability; and
requiring said person to complete the uncompleted categories on said form as part of completing a medical evaluation of the selected patient.

12. The method of claim 11 further comprising:
generating an electrocardiograph waveform for the patient; and
using a waveform analyzer to analyze the electrocardiograph waveform and generate the input signals.

13. The method of claim 12 wherein said particular heart condition is acute cardiac ischemia.

14. The method of claim 13 wherein the preselected range includes all possible probabilities above a preselected positive non zero lower limit.

15. The method of claim 14 wherein the preselected range only extends from about 5% to abut 55%.

16. The method of claim 13 wherein an empirically based mathematical model of actual clinical experience is used to compute the probability of acute cardiac ischemia.

17. The method of claim 16 wherein a regression model is used to compute the probability of acute cardiac ischemia.

18. The method of claim 17 wherein a multivariate logistic regression model is used to compute the probability of acute cardiac ischemia.

19. The method of claim 12 wherein the computing step also uses clinical data for the patient along with said to compute the probability of the patient having a particular heart condition.

* * * * *

UNITED STATES PATENT AND TRADEMARK OFFICE
CERTIFICATE OF CORRECTION

PATENT NO. : 5,276,612
DATED : Jan. 4, 1994
INVENTOR(S) : Harry P. Selker

It is certified that error appears in the above-indentified patent and that said Letters Patent is hereby corrected as shown below:

Column 1, line 38, replace "judgements" with --judgment--;

Column 5, line 51, replace "there at least three" with --there are at least three--;

Column 6, line 46, replace "judgement" with --judgment--;

Column 7, claim 1, line 7, after "regardless of", insert the following: --which of said patients is the selected patient and regardless of--;

Column 8, claim 11, line 4, after "measurements of the", insert --selected--.

Signed and Sealed this

Twenty-sixth Day of July, 1994

Attest:

BRUCE LEHMAN

Attesting Officer   Commissioner of Patents and Trademarks